United States Patent [19]

Caravel

[11] Patent Number: 6,083,262

[45] Date of Patent: Jul. 4, 2000

[54] SUPPLE IMPLANTABLE PROSTHESIS USED IN SURGERY FOR INCREASING THE VOLUME OF OR RECONSTRUCTING SOFT TISSUE, NOTABLY A BREAST PROSTHESIS, AND ITS METHOD OF MANUFACTURE

[76] Inventor: Jean-Baudoin Caravel, 52, Avenue Bosquet, 75007 Paris, France

[21] Appl. No.: 08/489,687

[22] Filed: Jun. 13, 1995

[30] Foreign Application Priority Data

Jun. 16, 1994 [FR] France ................................ 94 07375

[51] Int. Cl.[7] ................... A61F 2/12; A61F 2/04
[52] U.S. Cl. .................................. 623/8; 623/11
[58] Field of Search .................. 623/11, 12, 7, 623/8, 66; 128/DIG. 8, 21

[56] References Cited

U.S. PATENT DOCUMENTS

| | | | |
|---|---|---|---|
| 3,559,214 | 2/1971 | Pongman | 623/8 |
| 5,158,573 | 10/1992 | Berg | 623/11 |
| 5,192,326 | 3/1993 | Bao et al. | 623/11 |
| 5,246,454 | 9/1993 | Peterson | 623/8 |
| 5,258,028 | 11/1993 | Ersek et al. | 623/11 |
| 5,383,929 | 1/1995 | Ledergerber | 623/8 |
| 5,425,762 | 6/1995 | Muller | 623/8 |

*Primary Examiner*—David Isabella
*Attorney, Agent, or Firm*—Westman, Champlin & Kelly, P.A.

[57] ABSTRACT

The breast prosthesis has a bag 1 made of a silicone polymer fitted with a closure disc 2 which is head sealed onto it. The bag 1 contains silicone polymer balls 3 of 2 mm diameter and which fill to the whole bag 1 whilst being in contact with one another and forming interstices 4 between them filled with physiological saline solution.

11 Claims, 2 Drawing Sheets

SUPPLE IMPLANTABLE PROSTHESIS USED IN SURGERY FOR INCREASING THE VOLUME OF OR RECONSTRUCTING SOFT TISSUE, NOTABLY A BREAST PROSTHESIS, AND ITS METHOD OF MANUFACTURE

BACKGROUND OF THE INVENTION

The present invention concerns supple implantable prostheses used in surgery for increasing the volume of, modifying and repairing body shapes. The main example is the breast prosthesis but the invention also concerns calf, testicle and buttock prostheses and any other prosthesis intended to replace or simulate soft tissue.

A known prosthesis comprises a deformable bag made from a biocompatible material and containing a silicone gel. In spite of its remarkable properties of suppleness and adaptation due to the fact that the silicone gel has more or less the same density and the same consistency as human soft tissue, this prosthesis is prohibited by many laws because the silicone gel passes through the bag and spreads throughout the body, where it is liable to cause serious problems.

A prosthesis similar to that which has just been described is also known, the difference being that a polysaccharide gel is used in place of the silicone gel. The drawback of this prosthesis is that, when the prosthesis is in place, the polysaccharide gel is liable to absorb water and cause undesirable swelling and then deflate along with osmotic exchange. Thus over time the volume of the breast of the patient varies.

A prosthesis comprising a bag filled with a physiological saline solution has also been proposed, with the drawback that the bag gradually empties due to the permeability of the solution through the membrane and so the prosthesis collapses, also with the drawback that the bag can empty completely if there is a leak.

In U.S. Pat. No. 3,986,213, a breast prosthesis comprising a bag filled with silicone gel is described, with the drawbacks described above, and whose density is reduced by a dispersion of glass or epoxy microspheres so as to reduce the total density of the prosthesis.

In European patent application No. 322 194 a bag containing elements sustaining a pressure and which are filled with a gas so as to obtain a damping effect is described among others with reference to FIG. 23. This damping effect can be supplemented by a structure in the form of a spring inside each element. In addition to this prosthesis being very complicated to manufacture and therefore prohibitively expensive, when the elastic force of the spring inside each element sustaining compression is added to the force due to the gas pressure inside this element, the membrane constituting the bag becomes too firm to constitute the surface of an artificial breast unless it is accepted that, when these elements burst or lose their fluid due to the permeability of the membranes which constitute them, they collapse. Then, however, the volume of the breast is not maintained.

SUMMARY OF THE INVENTION

The invention overcomes these drawbacks by means of a prosthesis which is particularly inexpensive to manufacture and which, without excluding it, does not require the use of a gel with the drawbacks of migration in the body or of swelling and which, nevertheless, enables the volume, notably of the breast, to be kept sufficiently constant.

The prosthesis comprises a deformable bag made of a biocompatible material and containing solid elements forming interstices between them, the largest dimension of each element being less than 8 mm. According to the invention, the solid elements are in contact with one another so that they can slide against one another and fill substantially the whole bag.

It could seem paradoxical a priori to use solid and therefore relatively hard elements in a soft tissue prosthesis and, moreover, to ensure that they fill substantially the whole of the bag, so that it might be feared that the prosthesis would become hard but, by ensuring that the largest dimension of each element is less than 8 mm and preferably 4 mm, it is found that, by ensuring, through all these solid elements and the fact that they occupy all the bag, that the volume of the prosthesis remains substantially constant, the ability of the small rigid solid elements to slide against one another if subjected to a force gives the prosthesis sufficient suppleness and deformability.

In the preferred version of the invention, the material consists of small smooth spherical balls, the optimum size of which is between 2 mm and 4 mm in diameter, made of a solid silicone polymer of medical quality, which for a long time has been recognized as being perfectly biocompatible. The spaces left empty between the balls are filled with a physiological saline solution to facilitate sliding. The quantity of the solution is about 42% to 45% of the volume of the prosthesis, which enables the spaces left empty between the balls to be filled without causing any notable increase in its volume. The advantage of such a configuration is that:

in the event of the liquid leaking through the bag, the volume of the implant is maintained by the solid elements and the loss of liquid will be compensated for by a physiological exudation of the tissues in the exclusion space created by the implant, in the event of a traumatic rupture of the prosthesis, the elements, which could be extracted surgically, will not be liable to migrate throughout the body and will be well tolerated without causing inflammatory reactions as is the case with silicone gel.

By way of a non-limitative example, a breast prosthesis of 150 $cm^3$ made from a silicone polymer bag filled with spherical balls of 2 mm in diameter requires a quantity of physiological saline solution of about 64 to 66 $cm^3$ to fill completely the spaces left empty between the balls without causing an increase in the volume. The suppleness of such a prosthesis is very close to that of a prosthesis filled with silicone gel and does not give the impression of shaking as does a prosthesis filled solely with saline solution.

By using balls of 3 mm diameter and in a casing of the same volume, 64 to 66 $cm^3$ of the solution is also needed to completely fill the empty spaces and these alone: a suppleness and elasticity sufficiently close to the preceding prosthesis is then obtained.

With balls of 5 mm diameter in a casing of 150 $cm^3$, there still needs to be approximately the same amount of saline solution to fill the empty spaces completely. The prosthesis is less supple and the granular appearance of the latter can be clearly felt; it can be used where the thickness of the covering tissues is considerable and where a firmer texture is sought as in retromuscular positions for, for example, a buttock prosthesis.

In other advantageous versions of the invention:

the substance constituting the solid elements is an acrylic polymer, any other biocompatible plastic, ceramic or a biocompatible metal, the shape of the solid elements is polyhedral or ovoid, and their surface is smooth or alveolar or irregular so long as they slide against each other satisfactorily, the optimum size of the elements is between 2 and 4 mm, should not be more than 15 mm but could be less than 1 mm, the solid elements are solid or hollow, the spaces or interstices left empty between the solid elements are filled with a gas, a liquid, a solution or a liquid suspension, or a gel other than a silicone gel, when they are at body temperature, provided that they are non-toxic and biocompatible.

The above prostheses defined by the invention are comprised of a bag or casing which is smooth or textured or covered with polyurethane, which can be made of a silicone polymer as in the prostheses filled with gel, the filling being done during manufacture. They can be inflatable, the casing being put in place when empty and filled with the substance during the operation by injection through a valve which forms part of the casing, the valve subsequently being closed by heat sealing a closure disc.

Other protheses coming within the scope of the invention can be made up of one or more bags defining several separate compartments, one or more of which are filled with the substance defined in the invention. The most common examples which, however, are not limitative are:

breast prosthesis with a double casing defining an internal and a peripheral compartment, one of which is filled beforehand and the other inflated during the operation; the substance described by the invention can occupy one or both compartments;

the expansion prosthesis, one of whose compartments can be increased progressively in volume in successive operations by injecting saline solution through the skin with a needle puncturing a specially designed point on the prosthesis in communication with the compartment to be inflated in order to obtain a progressive distension of the tissues.

The invention also relates to a method for manufacturing a prosthesis which consists of filling substantially the whole of a deformable bag made from a biocompatible material, through an opening made in the bag, with solid elements forming interstices between them and which are in contact with one another so that they can slide against each other, the largest dimension of each element being less than 8 mm, and closing the bag by heat sealing a disc over the opening.

BRIEF DESCRIPTION OF THE DRAWINGS

In the accompanying drawing, given solely by way of example,

FIG. 3A shows prosthesis 1' divided laterally from side-to-side with divider 5 while FIG. 3B shows prosthesis 1" divided from top to bottom with wall 6. Of course, other configurations can be used.

DETAILED DESCRIPTION OF THE PREFERRED EMBODIMENTS

Figure 1:
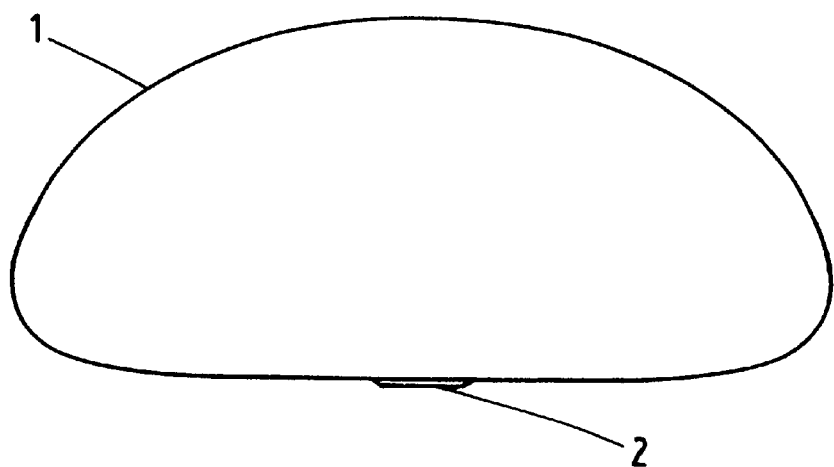
FIG. 1 is an elevation view of a breast prosthesis according to the invention and FIG. 2 is a partial view in cross section thereof.
Figure 2:
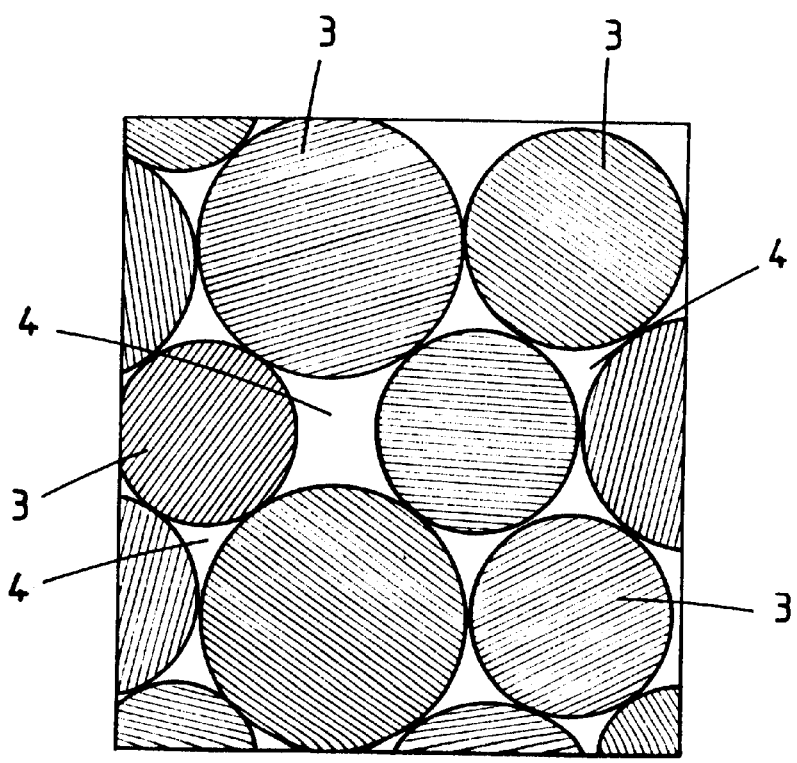
Figure 3A:
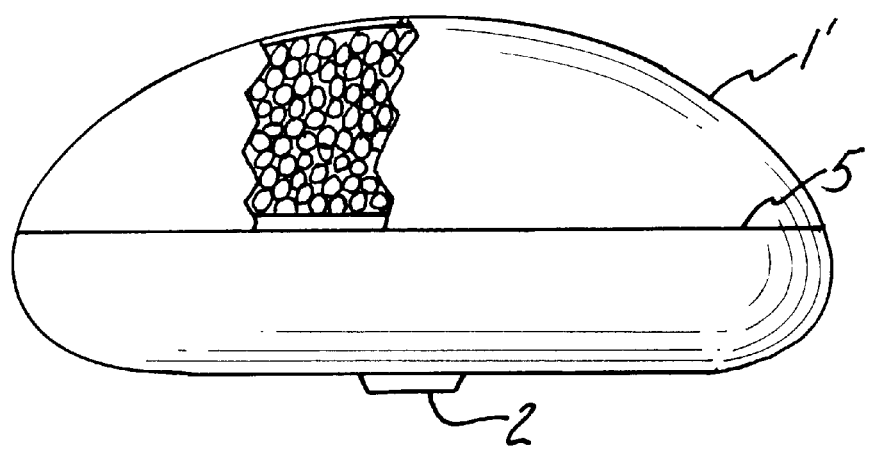
FIGS. 3A and 3B are side and top views of two different embodiments of the present invention showing the prosthesis divided into compartments.
Figure 3B:
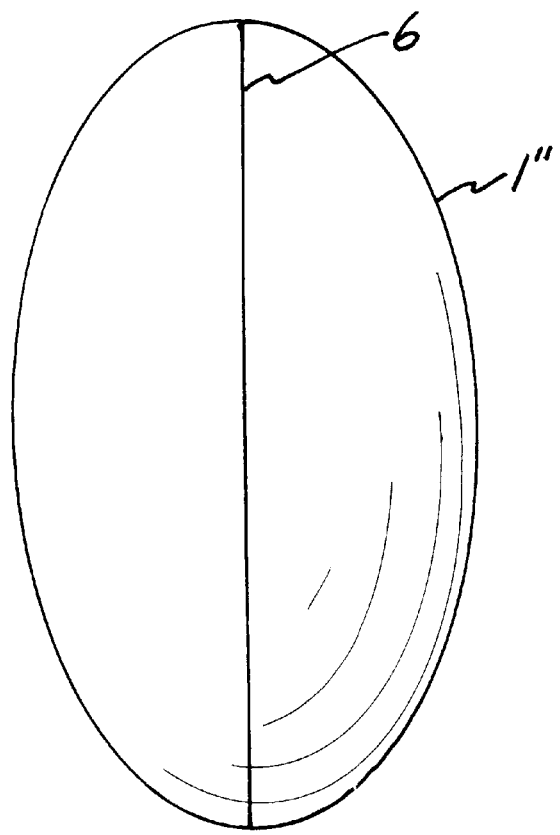

The breast prosthesis has a bag 1 made of a silicone polymer fitted with a closure disc 2 which is heat sealed onto it.

The bag 1 contains silicone polymer balls 3 of 2 mm diameter and which fill the whole bag 1 whilst being in contact with one another and forming interstices 4 between them filled with physiological saline solution.

What is claimed is:

1. An implantable prosthesis comprising a deformable bag made of a biocompatible material and containing rigid elements forming interstices, the rigid elements having a largest dimension of less than 8 mm, wherein the rigid elements are in contact with one another and are formed to be slidable against one another and substantially completely fill the bag.

2. An implantable prosthesis according to claim 1, wherein the rigid elements are made of a silicone polymer.

3. An implantable prosthesis according to claim 1, wherein the rigid elements are selected from the group consisting of an acrylic polymer, a biocompatible plastic, ceramic, and a biocompatible metal.

4. An implantable prosthesis according to claim 1, wherein the rigid elements are in the form of one selected from the group consisting of spherical balls, ovoids, and polyhedrons with a surface selected from the group consisting of a smooth, an alveolar, and an irregular surface.

5. An implantable prosthesis according to claim 1, wherein the rigid elements are solid.

6. An implantable prosthesis according to claim 1, wherein the interstices are filled with a fluid.

7. Prosthesis according to claim 6, wherein the fluid is physiological saline solution.

8. An implantable prosthesis according to claim 1, wherein the bag has a plurality of compartments, and at least one of the plurality of compartments contains the rigid elements forming interstices.

9. An implantable prosthesis according to claim 1 wherein the rigid elements are hollow.

10. An implantable prosthesis according to claim 1 wherein the interstices are filled with a gel.

11. An implantable prosthesis according to claim 1 wherein the rigid elements are formed of a single material.

* * * * *